United States Patent [19]

Lamberti et al.

[11] Patent Number: 4,623,483
[45] Date of Patent: Nov. 18, 1986

[54] METHOD FOR IMPROVING WATER SOLUBILITY OF SURFACTANTS USING NOPOL DERIVED SULFONATES

[75] Inventors: Vincent Lamberti, Upper Saddle River; Eddie N. Gutierrez, Fort Lee, both of N.J.

[73] Assignee: Lever Brothers Company, New York, N.Y.

[21] Appl. No.: 704,990

[22] Filed: Feb. 25, 1985

Related U.S. Application Data

[62] Division of Ser. No. 583,557, Feb. 27, 1984, Pat. No. 4,530,801.

[51] Int. Cl.[4] .................... C11D 3/34; C11D 1/22
[52] U.S. Cl. ..................... 252/545; 252/549; 252/555; 252/558; 252/363.5; 252/DIG. 14
[58] Field of Search ............ 252/549, 555, DIG. 14, 252/545, 363.5, 558; 260/503

[56] References Cited

U.S. PATENT DOCUMENTS

| | | |
|---|---|---|
| 2,220,678 | 11/1940 | Cromwell et al. .................... 260/98 |
| 2,243,331 | 5/1941 | de Simo et al. .................... 260/503 |
| 2,318,036 | 5/1943 | Werntz .................... 260/503 |
| 3,332,880 | 7/1967 | Kessler et al. .................... 252/555 |
| 3,929,680 | 12/1975 | Arai et al. .................... 252/542 |
| 4,137,257 | 1/1979 | Traynor .................... 260/503 |
| 4,224,240 | 9/1980 | Kane et al. .................... 260/503 |
| 4,283,347 | 8/1981 | Kane et al. .................... 260/429.9 |
| 4,524,022 | 6/1985 | Naylor .................... 252/548 |
| 4,524,023 | 6/1985 | McCoy et al. .................... 252/548 |

OTHER PUBLICATIONS

Traynor et al., J. Org. Chem., vol. 44, p. 1557 (1979).

*Primary Examiner*—Prince E. Willis
*Attorney, Agent, or Firm*—Milton L. Honig; James J. Farrell

[57] ABSTRACT

The p-menth-6-ene-7-methylol-2-sulfonic and p-menthane-7-methylol-2-sulfonic acids and their alkali metal, alkaline earth metal, ammonium and alkylolammonium salts are disclosed. A process is provided for preparing the ammonium salts thereof. A method is presented for increasing the solubility of an only partially water-soluble material using these sulfonic salts as a hydrotrope.

3 Claims, No Drawings

METHOD FOR IMPROVING WATER SOLUBILITY OF SURFACTANTS USING NOPOL DERIVED SULFONATES

This is a divisional application of Ser. No. 583,557 filed Feb. 27, 1984 which matured into U.S. Pat. No. 4,530,801.

BACKGROUND OF THE INVENTION

1. Field of the Invention

The invention relates to novel terpene derived sulfonates, their use as hydrotropes and processes for their preparation.

2. The Prior Art

Many aqueous compositions contain organic components of poor water solubility. Hydrotropes are formulated into these liquids to increase the aqueous solubility of the hydrophobic organic components. Commonly employed hydrotropes include the salts of toluene, xylene or cumene sulfonates. While these commercial compounds perform satisfactorily, there is a need for lower cost alternatives, especially materials not derived from petrochemical feedstocks.

Among the relatively low-cost renewable raw materials is turpentine, an extract of pine trees. Major components of turpentine are $\alpha$- and $\beta$-pinenes. When reacted with pyrosulphuryl chloride, $\alpha$ and $\beta$-pinenes yield sulfonate compounds as in U.S. Pat. No. 2,220,678. Traynor et al, *J. Org. Chem.*, Vol. 44, 1557, 1979, reports that sodium p-menth-6-ene-2-sulfonate can be formed from the dehydration of the reaction product between sodium sulfite and the $\alpha$-pinene derivative limonene oxide. This publication further discloses that $\beta$-pinene will react with sodium bisulfite to form sodium p-menth-1-ene-7-sulfonate. Little has been reported concerning the utility of these sulfonated pinene derivatives. U.S. Pat. Nos. 4,224,240 and 4,283,347, however, mention the possible utility of p-menth-1-ene-7-sulfonate salts as detergents and surfactants.

Reaction of $\beta$-pinene with formaldehyde forms the very useful intermediate 6,6-dimethyl-bicyclo[3.1.1]hept-2-ene-2-ethanol, commonly referred to as Nopol. Little is known of sulfonated Nopol derivatives.

Accordingly, it is an object of this invention to describe novel sulfonated Nopol derivatives.

Furthermore, it is an object of this invention to provide processes for the manufacture of certain sulfonated Nopol derivatives.

Another object of this invention is to provide a method for solubilizing only partially water-soluble compounds in aqueous formulations by means of Nopol derived sulfonate hydrotropes.

SUMMARY OF THE INVENTION

The p-menth-6-ene-7-methylol-2-sulfonic and p-menthane-7-methylol-2-sulfonic acids and their alkali metal, alkaline earth metal, ammonium and alkylolammonium salts are hereby disclosed.

Furthermore, a process is provided for preparing the ammonium salts of p-menth-6-ene-7-methylol-2-sulfonic and p-menth-7-methylol-2-sulfonic acids comprising:

(a) adding ammonium bisulfite to a stirred aqueous or an aqueous-organic co-solvent dispersion of Nopol, the pH being maintained above 5.5 or below 5.3 to obtain predominantly either trans or cis isomers, respectively;

(b) removing solvent from the reaction mixture; and (c) optionally, hydrogenating the resultant products.

Finally, a method is disclosed for increasing the solubility of an only partially water-soluble material comprising combining with said material in water a hydrotrope selected from the group consisting of the alkali metal, alkaline earth metal, ammonium and alkylolammonium salts of p-menth-6-ene-7-methylol-2-sulfonic and p-menthane-7-methylol-2-sulfonic acids.

DETAILED DESCRIPTION OF THE INVENTION

The novel sulfonates I and II have been prepared and found to be effective hydrotropes in aqueous media. These compounds are identified by the following structural formulas:

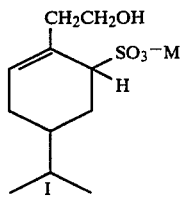 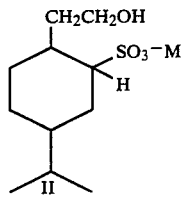

where M is an alkali metal, alkaline earth metal, ammonium or alkylolammonium cation.

Compound I is synthesized from 6,6-dimethylbicyclo[3.1.1]hept-2-ene-2-ethanol (Nopol). Nopol is derived from a Prins reaction between $\beta$-pinene and formaldehyde. The procedure involves incremental additions of alkali metal or ammonium bisulfites to Nopol suspended in aqueous or mixed aqueous-organic co-solvent solutions in the presence of air or a free radical initiator. Ammonium sulfite may be used by decomposition in situ as a source of bisulfite. In general, the optimum pH for these reactions is between about 5 to 6.

Where ammonium salts of sulfite or bisulfite are employed, oxygen is the preferable free radical initiator. These reactions readily occur at atmospheric pressure.

Bisulfite reactions are preferably initiated by organic or inorganic perioxides. Representative of the former type free radical initiators are tert-butyl peroxide, benzoyl peroxide, cumene hydroperoxide, tetralin hydroperoxide, isopropylbenzene hydroperoxide, acetyl peroxide, urea peroxide, methylethyl ketone peroxide, diisopropyl ether peroxide, diisopropyl peroxy dicarbonate, and, preferably tert-butyl peroxy benzoate. Inorganic initiators such as hydrogen peroxide, hydrazine sulphate, sodium percarbonate and sodium persulphate are also useful. Organic diazo initiators, such as azobisisovaleronitrile and azobisisobutyronitrile, may similarly be employed. The free radical initiators are preferably combined with the sulfite or bisulfite and incrementally added to the Nopol. Generally, from about 0.1 to about 10 mole %, based on moles Nopol, of the free radical initiator are used in the reaction mixture. Additionally, ultraviolet radiation may serve to establish the free radical conditions, including when an ultraviolet photo-initiator is added to the reaction mixture.

Although water can be used as the exclusive solvent, mixed water-organic co-solvent systems are preferred. The organic co-solvents should be non-reactive in the process. Such solvents include alcohols, ethers, glycol ethers, esters, glycols, amines, amino alcohols and mixtures thereof. A combination of water with isopropanol or ethanol is preferred. Mixed aqueous-organic co-solvent systems may be combined in ratios ranging from 100:1 to 1:100. Preferably, the ratio of water to co-solvent should range from about 1:4 to 1:1. Water is present to assist the solubilization of the sulfite or bisulfite salt. Organic co-solvent is present for solubilizing the Nopol. The amount of solvent, either water, organic co-solvent or mixtures thereof, relative to Nopol will range from 100:1 to 1:100, respectively.

Reaction temperatures should range from at least 40° C. to about 300° C. Preferably, the range should be from about 80° C. to 150° C.

Relative molar ratios of sulfite or bisulfite to Nopol can range broadly from about 2:1 to 0.8:1. Preferably, their relative amounts should range from about 0.95:1 to 1.4:1, sulfite or bisulfite to Nopol, respectively.

Ammonium bisulfite provides better yields than ammonium sulfite, i.e., 28% versus 91% yield. Aqueous 45% ammonium bisulfite solutions may be utilized at the commercially available pH of 5.0–5.2 or adjusted to pH 5.6–6.0 with ammonia. On completion of the reaction, solvent is removed. At pH above 5.5, ammonium bisulfite reacts stereospecifically with Nopol to form the trans isomer of I. Lowering pH to 5.3 or below affords cis isomer in significant amounts. Cis isomer separates as a resinous dark yellow material. The trans compound is crystalline. Furthermore, the cis isomer appears to be more susceptible to auto-oxidation. Hydrogen peroxide rapidly attacks cis isomer while the trans form is unaffected.

Compound I can be converted to its saturated analog II through hydrogenation. A variety of hydrogenation methods and catalysts can be employed. Both soluble and heterogeneous catalysts are suitable. Among the heterogeneous variety are included platinum, palladium, rhodium, ruthenium, iridium and nickel, each metal being supported on suitable substrates to facilitate in the uptake of gaseous hydrogen.

Hydrogenation of I proceeds best at elevated pressures and temperatures. Raney nickel is the catalyst of choice. Temperatures in excess of 100° C. and pressures of 500 psig hydrogen and above are preferred operating conditions.

Sodium, potassium, alkaline earth metal and alkylolammonium salts of I and II may be obtained by treatment of the corresponding ammonium salt by passage through an ion exchange column and neutralization of the liberated sulfonic acid with the appropriate base (e.g., sodium hydroxide, potassium hydroxide and alkylolamines such as mono-ethanolamine, diethanolamine and triethanolamine).

Sulfonate II has better storage stability than its unsaturated precursor. Upon prolonged storage, compound I develops a yellow color. No color degradation is noted for II. Presumably, oxygen attack on the double bond produces chromophoric products in the unsaturated compound.

Compounds I and II are here shown to be effective hydrotropes for solubilizing only partially water-soluble materials into aqueous systems. Hydrotropes are commercially important, in particular, as components in aqueous cleaning compositions. These compositions frequently contain surfactants such as anionic, nonionic, cationic, zwitterionic or amphoteric actives or mixtures thereof. These surfactants are set forth in "Surface Active Agents and Detergents" by Schwartz, Perry & Berch, Vol. II, Interscience Publishers, Inc., 1958, and "Synthetic Detergents" by A. Davidsohn and B. M. Milwidsky, George Goodwin Ltd. (London) and John Wiley & Sons, N.Y., 1978; both herein incorporated by reference. These surfactants are generally employed at from 1% to 50% by weight of the total cleaning formulation.

STABILITY PERFORMANCE EVALUATION

A measure of the effectiveness of a hydrotrope is the amount required to stablize a liquid composition undergoing freeze-thaw cycling.

The procedure for evaluating freeze-thaw stability involves subjecting a sample in a glass jar to six controlled freeze-thaw cycles between 0° F. and 70° F. Typically, inspection of samples is performed after each 1, 2, 3 and 6 cycles. Cycling time between 0° F. and 70° F. is 24 hours, except over weekends when temperature is maintained at 70° F. for 48 hours. Six hours are necessary for the temperature in the room to drop from 70° F. to 0° F. and 4 hours to rise from 0° F. to 70° F. These cycles are thought to simulate the most extreme conditions for storage and transportation of hydrotrope containing commercial products during winter months.

The following examples will more fully illustrate the embodiments of this invention. All parts, percentages and proportions referred to herein and in the appended claims are by weight unless otherwise indicated.

EXAMPLE 1

A typical light duty liquid dishwashing formulation is outlined in Table I. Into this base formulation were incorporated the various hydrotropes of this invention.

TABLE I

| Light Duty Liquid Detergent Base Composition | | |
|---|---|---|
| | % Actives by Weight in Formula | |
| Components | Formula A | Formula B |
| Ammonium linear $C_{10}$–$C_{15}$ alkylbenzene sulfonate | 24 | 30 |
| Ammonium linear $C_{12}$–$C_{14}$ alcohol triethoxysulfate | 5 | 5 |
| Lauric diethanolamide | 3 | — |
| Hydrotrope* | — | — |
| Magnesium chloride | — | 0.5 |
| Water | to 100 | to 100 |

*Identity and amounts as per following Examples.

TABLE II

| Heavy Duty Built Liquid Laundry Detergent | |
|---|---|
| Components | % Active by Weight in Formula |
| Sodium linear $C_{10}$–$C_{15}$ alkylbenzene sulfonate | 17 |
| Sodium nitrilotriacetic acid | 13 |
| Hydrotrope* | — |
| Water | to 100 |

*Identity and amounts as per following Examples.

EXAMPLE 2

Unsaturated and saturated sulfonates, I and II, were separately incorporated as a hydrotrope into the base aqueous liquid detergent formula A. Several concentration levels were evaluated. Results are recorded in Table III. Data therein indicates that 6% of either the unsaturated or saturated sulfonated Nopol is sufficient to provide freeze-thaw stability toward formula A. Compounds I and II are most efficient as hydrotropes than the reference, ammonium xylene sulfonate.

TABLE III

Freeze-Thaw Stability of Sulfonated Nopol Derivatives

| Sample No. | Hydrotrope* | Concentration (% Weight) | Freeze-Thaw Stability 6 cycles at 0–70° F. |
|---|---|---|---|
| 1 | Ammonium xylene sulfonate (Control) | 8 | Stable |
| 2 | Ammonium xylene sulfonate (Control) | 6 | Two Phases |
| 3 | Compound I | 4 | Two Phases |
| 4 | Compound I | 6 | Stable |
| 5 | Compound I | 8 | Stable |
| 6 | Compound II | 6 | Stable |
| 7 | Compound II | 7 | Stable |
| 8 | Compound II | 8 | Stable |
| 9 | Compound II | 9 | Stable |

*Compounds I and II evaluated as the ammonium salt.

EXAMPLE 3

This example illustrates the freeze-thaw stability of compounds I and II incorporated into base formula B. Table IV tabulates the hydrotrope performance. Ammonium xylene sulfonate in formula B is a more efficient hydrotrope than I.

TABLE IV

Freeze-Thaw Stability Performance of Unsaturated Sulfonated Nopol

| Sample No. | Hydrotrope* | Concentration (% Weight) | Freeze-Thaw Stability 6 cycles at 0–70° F. |
|---|---|---|---|
| 1 | Ammonium xylene sulfonate (Control) | 9 | Clear |
| 2 | Compound I | 6 | Two Phases |
| 3 | Compound I | 7 | Two Phases |
| 4 | Compound I | 8 | Two Phases |
| 5 | Compound I | 9 | Two Phases |

*Compound I evaluated as the ammonium salt.

EXAMPLE 4

An illustration of hydrotropic performance of Compound I (ammonium salt) in a built heavy duty liquid composition is herein provided. The data in Table V indicates that I is a more efficient hydrotrope than sodium xylene sulfonate. It is also apparent that mixtures of sodium xylene sulfonate with I interact to provide unexpectedly superior results. The compositions evaluated were in accordance with the formula outlined in Table II.

TABLE V

| Sample | Hydrotrope (% weight) | Physical Stability |
|---|---|---|
| 1 | Sodium xylene sulfonate (8%) | 20% separated top |
| 2 | Sodium xylene sulfonate (10%) | 15% separated top |
| 3 | Sodium xylene sulfonate (8%) Compound I (1%) | Clear with schlieren |
| 4 | Sodium xylene sulfonate (8%) Compound I (2%) | Traces of separated top |
| 5 | Compound I (6%) | Clear with schlieren |
| 6 | Compound I (8%) | Trace of separated bottom |

EXAMPLE 5

Comparisons between Compound I (sodium salt) and sodium xylene suflonate in the formulation of Table II is detailed in Table VI. Approximately 9% of I was required to achieve stability at room temperature. Sodium xylene sulfonate was required only at 6% to achieve stability at the same temperature.

TABLE VI

| Hydrotrope (Weight %) | Stability Room Temperature | Stability 35° F. overnight | Freeze-Thaw (0–70° F.) 6 cycles |
|---|---|---|---|
| Sodium xylene sulfonate (6%) | Clear | Two Phases | — |
| Sodium xylene sulfonate (8%) | Clear | Clear | About 8% gel on top |
| Compound I (8%) | Two Phases | Two Phases | — |
| Compound I (9%) | Clear | Two Phases | — |
| Compound I (10%) | Clear | Clear | Stable (Clear) |

EXAMPLE 6

Preparation of Ammonium p-menth-6-ene-7-methylol-2-trans-sulfonate

Ammonium Sulfite Method

Into a 2 liter, 3-neck flask equipped with stirrer and reflux condenser were placed 600 grams isopropanol, 200 grams water and 166 grams (1 mole) Nopol. To the refluxing mixture were added 134 grams aqueous ammonium sulfite (1 mole) at the rate of 13.4 grams per hour. The solution was refluxed for a total of 14 hours. Then it was evaporated to dryness. The residue was dissolved in isopropanol, filtered and the resulting filtrate evaporated to dryness. A product weighing 102 grams (74% active) was obtained in 28% yield.

EXAMPLE 7

Preparation of Ammonium p-menth-6-ene-7-methylol-2-trans-sulfonate

Ammonium Bisulfite Method 1

In a 500 ml flask, equipped with a magnetic stirrer, were placed 66.4 grams (0.4 mole) Nopol, 100 ml ethanol and 100 ml water. To the stirred mixture was added 110 grams (45%) ammonium bisulfite solution adjusted with ammonia to pH 5.6 to 6.0. The mixture was stirred at 40°–45° C. for 24 hours.

Solvents were distilled off and the residue extracted with 300 ml ether. About one gram of Nopol was recovered. The residue was then dissolved in 300 ml isopropanol. Insoluble materials weighing 7.5 grams were removed by filtration. Isopropanol was removed by vacuum distillation leaving a residue which was further dried over phosphorus pentoxide. A product weighing 109 grams (88.5% active) was obtained in 91% yield.

Ammonium Bisulfite Method 2

In a liter flask equipped with magnetic stirrer were placed 420 ml isopropanol, 240 ml water and 66 grams (0.4 mole) Nopol. While the solution was being stirred, 105 grams (45%) ammonium bisulfite solution (pH5.6–6.0) was added. The solution was stirred for 24 hours. Solvents were evaporated in vacuo and residue dissolved in methanol. The methanol solution was filtered to remove inorganics. Filtrate was evaporated to give 102 grams residue. The residue was dissolved in hot isopropanol. Recrystallization gave 94 grams (99.2% purity) of a crystalline product indicating a yield of 88.7%. The NMR analysis exhibited the following spectrum: $CH_3$ (doublet, 0.75–0.90$\delta$, coupling constant 6 Hz); $CH_2$ (multiplet, 1.20–2.70$\delta$); CH (multiplet, 1.20–2.70δ); CH (multiplet, 3.45–75δ); CH$_2$ (multiplet centered at 3.73δ) and CH (multiplet, 5.72–6.00δ).

Ammonium Bisulfite Method 3

In a 1-liter, 3-neck Morton flask were placed 99.5 grams (0.6 mole) Nopol, 125 ml ethanol and 50 ml water. The solution was de-aerated with nitrogen gas using a gas dispersion tube. The solution was heated to 70° C. with vigorous agitation.

In an addition funnel were combined at 10° C., 110 grams (0.5 mole) 45% ammonium bisulfite solution and 17.6 grams concentrated ammonia. This solution was brought to room temperature and added slowly to the contents of the Morton flask with concurrent addition of 1.38 grams (8.4 mmol) azobisisovaleronitrile in 25 ml aqueous ethanol. Addition was complete in 45 minutes. Thereafter, the mixture was stirred a further 6.5 hours at 70° C.

The above solution was steam distilled to remove Nopol. Thereafter, the remaining aqueous solution was evaporated to dryness leaving behind the product. This material weighed 124.8 grams (70% purity) corresponding to a 66% yield.

EXAMPLE 8

Preparation of Ammonium p-menth-6-ene-7-methylol-2-cis-sulfonate

Into a liter flask equipped with a magnetic stirrer were placed 150 ml ethanol and 83 grams Nopol (0.5 mole. To this solution was added 156 grams (45%; 0.7 mole) ammonium bisulfite having pH 5.0–5.1. The mixture was stirred at 40° C. for 24 hours.

Ammonium hydroxide, 16 grams, was added to the reactor bringing pH to 6.8–7.0. Ethanol was distilled and the aqueous solution extracted three times with 200 ml chloroform. The aqueous solution was evaporated to a heavy syrup. Methanol, 350 ml, was added. The solution was allowed to stand for 30 minutes and filtered to remove inorganics. Methanol was evaporated from the solution affording a syrup that was dried over phosphorus pentoxide. A product weighing 134 grams was obtained. Unreacted Nopol, 18 grams, was recovered from the chloroform solution. The product was stored under nitrogen to prevent oxidation. NMR analysis indicated product purity of 72.6% (57.3% yield). The NMR spectrum of the product was as follows: CH$_3$ (doublet, 0.80–0.92δ, coupling constant 2.1 Hz); CH$_2$ (multiplet, 1.2–2.60δ); CH (multiplet, 1.20–2.60δ); CH (multiplet, 3.45–3.70δ); CH$_2$ (multiplet centered at 3.45–3.75δ) and CH (multiplet, 5.65–5.90δ).

EXAMPLE 9

Preparation of Ammonium p-menthane-7-methylol-sulfonate

Seventy grams of ammonium-p-menth-6-ene-7-methylol sulfonate prepared as in Example 7 (Method 2) was stored overnight at 45°–50° C. over 500 ml water containing 50 grams Raney Nickel catalyst. The mixture was transferred to a one-liter Parr bomb. Raney Nickel, 12 grams, was added to the mixture. The bomb was sealed and flushed several times with hydrogen. Hydrogenation was performed at 125° C. under 500 psig of hydrogen for a period of 4 hours.

The mixture was removed from the bomb, filtered free of catalyst and allowed to stand. A very small amount of light brown solid, which crystallized out, was filtered before evaporating the filtrate to dryness. A total of 65 grams (100% purity) was obtained. The NMR spectrum consisted of: CH$_3$ (doublet, 0.80–1.00δ); CH$_2$ (multiplet, 1.00–2.30δ); CH (multiplet, 1.00–2.30δ); CH (multiplet, 2.94–3.20δ) and CH$_2$ (triplet centered at 3.57δ).

The foregoing description and examples illustrate selected embodiments of the present invention and in light thereof variations and modifications will be suggested to one skilled in the art, all of which are in the spirit and purview of this invention.

What is claimed is:

1. A method for increasing the solubilty of an only partially water-soluble material, said material being present in an amount of from 1% to 50% and selected from the group consisting of anionic, nonionic, cationic, zwitterionic, amphoteric surfactants and mixtures thereof, comprising combining with said material in water, in an effective amount to increase said solubility, a hydrotrope selected from the group consisting of the alkali metal, alkaline earth metal, ammonium and alkylolammonium salts of p-methy-6-ene-7-methylol-2-sulfonic acid and of p-menth-7-methylol-2-sulfonic acid.

2. A method according to claim 1 further comprising an ammonium, alkali metal, alkaline earth metal or alkylolammonium salt of an alkylbenzene sulfonic acid.

3. A method according to claim 1 wherein the concentration of said hydrotrope ranges from about 4% to about 10%.

* * * * *